US012599387B2

(12) United States Patent
Radford

(10) Patent No.: US 12,599,387 B2
(45) Date of Patent: Apr. 14, 2026

(54) EMERGENCY PROTOCOL RECEPTACLE FOR PUNCTURE WOUNDS

(71) Applicant: Jesse Radford, Pontotoc, MS (US)

(72) Inventor: Jesse Radford, Pontotoc, MS (US)

(73) Assignee: Jesse Radford, Pontotoc, MS (US)

( * ) Notice: Subject to any disclaimer, the term of this patent is extended or adjusted under 35 U.S.C. 154(b) by 405 days.

(21) Appl. No.: 18/233,727

(22) Filed: Aug. 14, 2023

(65) Prior Publication Data

US 2023/0389934 A1    Dec. 7, 2023

(51) Int. Cl.
A61B 17/12 (2006.01)
A61B 17/00 (2006.01)
A61M 25/10 (2013.01)

(52) U.S. Cl.
CPC A61B 17/12136 (2013.01); *A61B 2017/0065* (2013.01); *A61B 2017/00907* (2013.01); *A61B 2017/12004* (2013.01); *A61M 25/1018* (2013.01)

(58) Field of Classification Search
CPC .......... A61B 17/12136; A61B 17/0057; A61B 2017/0065; A61B 2017/00907; A61B 2017/12004; A61B 2017/00557; A61B 2017/00654; A61B 2017/00659; A61B 2017/00902; A61B 2090/037; A61M 25/1018
See application file for complete search history.

(56) References Cited

U.S. PATENT DOCUMENTS

| | | | | |
|---|---|---|---|---|
| 6,071,300 | A * | 6/2000 | Brenneman ........ | A61B 17/0057 606/213 |
| 6,296,657 | B1 * | 10/2001 | Brucker ............. | A61B 17/0057 606/213 |
| 10,952,710 | B2 * | 3/2021 | Blumenthal ....... | A61B 17/0057 |
| 12,213,656 | B2 * | 2/2025 | Blumenthal ....... | A61B 17/0057 |
| 2019/0015086 | A1 * | 1/2019 | Blumenthal ....... | A61B 17/0057 |
| 2021/0204925 | A1 * | 7/2021 | Blumenthal ....... | A61B 17/0057 |
| 2023/0389934 | A1 * | 12/2023 | Radford ........... | A61B 17/12136 |

* cited by examiner

*Primary Examiner* — Ryan J. Severson

(57) ABSTRACT

An emergency protocol receptacle is disclosed for puncture wounds that utilizes an endothermic reaction between non-toxic chemicals to achieve inflation for effective and faster coagulation of blood in puncture type wounds. The emergency protocol receptacle comprises a balloon, a powder capsule, and a depressible top cap. The balloon is configured to inflate due to the endothermic reaction between non-toxic chemicals to stop bleeding from a puncture wound. The powder capsule is packed inside the balloon for holding a specific amount of baking soda. The depressible top cap is fixed on top of the powder capsule for holding a specific amount of vinegar. The depressible top cap facilitates flow of the vinegar into the powder capsule when depressed, causing a mixture of the vinegar with the baking soda to initiate inflation of the balloon due to chemical reaction between the vinegar and the baking soda.

8 Claims, 17 Drawing Sheets

200

200

200

300

300

302

308

304

310

312

306

312

302

502

504

302

304

304

304

304

604

<u>700</u>

EMERGENCY PROTOCOL RECEPTACLE FOR PUNCTURE WOUNDS

BACKGROUND OF THE INVENTION

Field of Invention

The embodiments herein relate to a medical apparatus and, more particularly, to an emergency protocol receptacle that utilizes an endothermic reaction between non-toxic chemicals to achieve inflation for effective and faster coagulation of blood in puncture type wounds.

Background of the Invention

In general, accidental trauma and acute bleeding are major medical problems. Acute bleeding seriously threatens lives and health of patients. Uncontrolled bleeding accounts for more than 30% of all traumatic deaths worldwide, more than half of which takes place prior to the arrival of emergency care. At present, there are many commercial hemostatic agents, like tissue adhesives, glutaraldehyde cross-linked albumin, zeolite-based QuickClot, fibrin-based bandages, or gelatin-based hemostatic agents, which have high hemostatic efficiency on superficial bleeding wounds.

However, the above mentioned hemostatic agents are typically ineffective against deep wounds caused by caliber firearms, simple explosive devices in the battlefield, and everyday injuries. Further, by using commercial hemostatic agents there is a high chance of entry of foreign particles in the wound site that can cause infection.

Moreover, patients with coagulopathies such as haemophilia, diabetes, liver illness, or advanced cancer who lack clotting factors or have thrombin generation dysfunctions frequently exhibit delayed haemostasis, which raises the patient's risk of dying from excessive bleeding. Thus, coagulopathy and hemostasis in individuals with non-compressible hemorrhage represent two of the biggest hurdles.

At present, shape memory hemostatic materials are used for hemostasis of incompressible bleeding. The shape memory hemostatic materials are supplied to an internal bleeding site and subsequently expanded to stop bleeding following absorption of blood. Some shape memory hemostatic materials are used in an injectable wound treatment method, in which sterile cotton pellets are injected into the wound to absorb the bleeding. While having good performance in the domain of non-compressible hemostasis, the shape memory hemostatic agents nevertheless have several drawbacks. For instance, it takes more time for the shape memory hemostatic agents to carefully remove each sterile cotton pellet from the wound.

Further, shape memory polymer foams are not good at absorbing liquid and take more time to return to their previous form, which causes additional blood loss due to a delayed hemostasis. Shape memory materials are also less effective in coagulopathy patients hemostasis as there aren't any research that have examined the hemostatic effectiveness in coagulopathy models and patients with coagulopathy.

Therefore, there is a need for an emergency device that coagulates blood effectively and faster in puncture type wounds.

SUMMARY OF THE INVENTION

The following presents a simplified summary of the present disclosure in a simplified form as a prelude to the more detailed description that is presented herein.

Therefore, in accordance with embodiments of the invention, an emergency protocol receptacle is designed for puncture wounds that utilizes an endothermic reaction between non-toxic chemicals to achieve inflation for effective and faster coagulation of blood in puncture type wounds.

Preferably, the emergency protocol receptacle for puncture wounds comprises a balloon, a powder capsule, and a depressible top cap.

In a preferred embodiment, the balloon is attached to an adhesive platform, and the adhesive platform is designed with an opening at center. Preferably, the balloon is a transparent silicon balloon that inflates due to endothermic reaction between non-toxic chemicals.

In one embodiment, the powder capsule is packed inside the balloon through the opening of the adhesive platform. In specific, the powder capsule holds a specific amount of baking soda.

In another embodiment, the depressible top cap is fixed on top of the powder capsule upon the adhesive platform. The depressible top cap is configured to hold a specific amount of vinegar and facilitates a flow of the vinegar into the powder capsule when squeezed or depressed, allowing mixing of the vinegar with the baking soda to initiate inflation of the balloon due to chemical reaction between the vinegar and the baking soda. Thereafter, the inflated balloon halts exsanguination in the puncture type wounds.

In another embodiment, the powder capsule comprises a depressible top cap, a middle cap, and a powder pouch. The depressible top cap comprises a rubber gasket ring around the circumference of the depressible top cap to act as a seal for the vinegar. One or more spikes are protruded out from bottom of the depressible top cap. A guide rail is passed along a center of the depressible top cap for allowing the flow of the vinegar, when the depressible top cap is squeezed or depressed.

The middle cap comprises a plurality of insertion holes to connect with the spikes and the guide rail of the depressible top cap. In specific, the insertion holes of the middle cap comprises a rail insertion slot at center to receive the guide rail of the depressible top cap for the flow of the vinegar. The powder pouch holds the baking soda and the powder pouch is connected to the middle cap using a holder ring The holder ring of the powder pouch aids in attaching the powder pouch to the bottom of the middle cap. In specific, the powder pouch is a woven square of cloth for holding a specific amount of baking soda.

In a preferred embodiment, a foil divider is placed in between the middle cap and the powder pouch for separating the baking soda and the vinegar. In specific, the foil divider is punctured by the spikes of the depressible top cap through the insertion holes of the middle cap when pressure is applied on top of the depressible top cap. The punctures on the foil divider allow the flow of the vinegar into the powder pouch.

In one embodiment, the depressible top cap is connected to the middle cap through a spring. The spring is configured to avoid the chance of accidental activation of the emergency protocol receptacle by separating the depressible top cap from the foil divider.

These and other features, aspects, and advantages of the present invention will become better understood with reference to the following description and appended claims.

BRIEF DESCRIPTION OF THE DRAWINGS

Illustrative embodiments of the present invention are described herein with reference to the accompanying drawings, in which.

DETAILED DESCRIPTION

Figure 1:
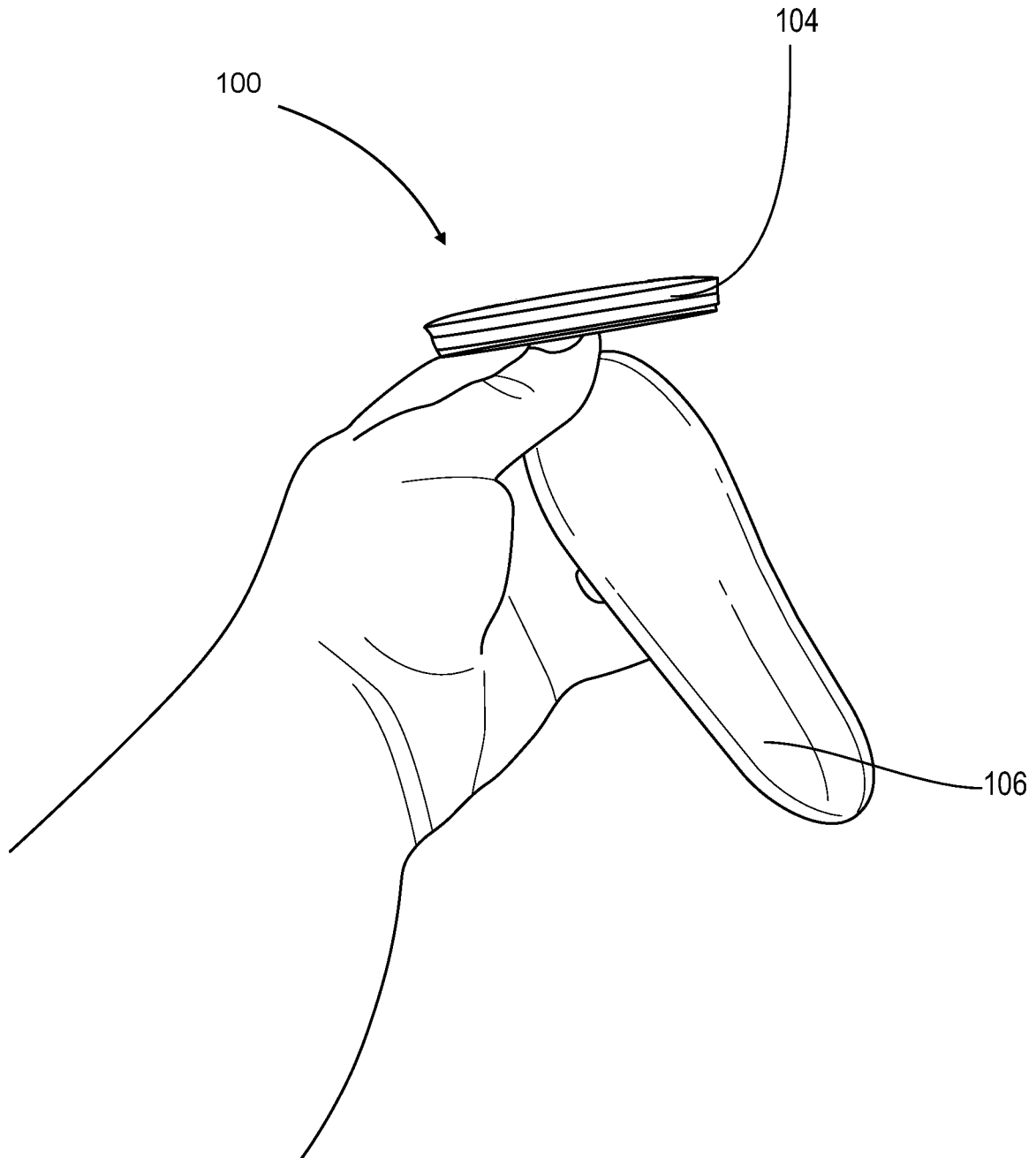
FIG. 1 is a prototype of an emergency protocol receptacle for puncture wounds, in accordance with embodiments of the invention.

For a further understanding of the nature and function of the embodiments, reference should be made to the following detailed description. Detailed descriptions of the embodiments are provided herein, as well as, the best mode of carrying out and employing the present invention. It will be readily appreciated that the embodiments are well adapted to carry out and obtain the ends and features mentioned as well as those inherent herein. It is to be understood, however, that the present invention may be embodied in various forms. Therefore, persons of ordinary skill in the art will realize that the following disclosure is illustrative only and not in any way limiting, as the specific details disclosed herein provide a basis for the claims and a representative basis for teaching to employ the present invention in virtually any appropriately detailed system, structure or manner. It should be understood that the devices, materials, methods, procedures, and techniques described herein are presently representative of various embodiments. Other embodiments of the disclosure will readily suggest themselves to such skilled persons having the benefit of this disclosure.

Reference will now be made in detail to the present preferred embodiments of the invention, examples of which are illustrated in the accompanying drawings. Wherever possible, the same reference numerals are used in the drawings and the description to refer to the same or like parts.

Referring to FIG. 1, a prototype of an emergency protocol receptacle 100 for puncture wounds is disclosed. FIGS. 1-6 illustrate the basic constructional details and operation of embodiments of the emergency protocol receptacle 100 for puncture wounds. The emergency protocol receptacle 100 comprises a depressible top cap 302, a powder capsule (not shown), and a balloon 106. The emergency protocol receptacle 100 utilizes an endothermic reaction between non-toxic chemicals to achieve inflation for effective and faster coagulation of blood in puncture type wounds.

The balloon 106 is inserted in a puncture wound and configured to inflate to stop bleeding at the wound site. The balloon 106 is attached to an adhesive platform 104. The adhesive platform 104 is designed with an opening (not shown) at center.

The powder capsule is packed inside the balloon 106. The powder capsule holds a specific amount of baking soda. The depressible top cap 302 is fixed on top of the powder capsule and upon the adhesive platform 104. The depressible top cap 302 is configured to hold a specific amount of vinegar, and the depressible top cap 302 facilitates enables a flow of the vinegar into the powder capsule when squeezed or depressed. The vinegar is then allowed to mix with baking soda to initiate inflation of the balloon 106 due to chemical reaction between the vinegar and the baking soda, as shown in FIG. 1. Thereby, the inflated balloon halts exsanguination in the puncture type wounds.

Figure 2A:
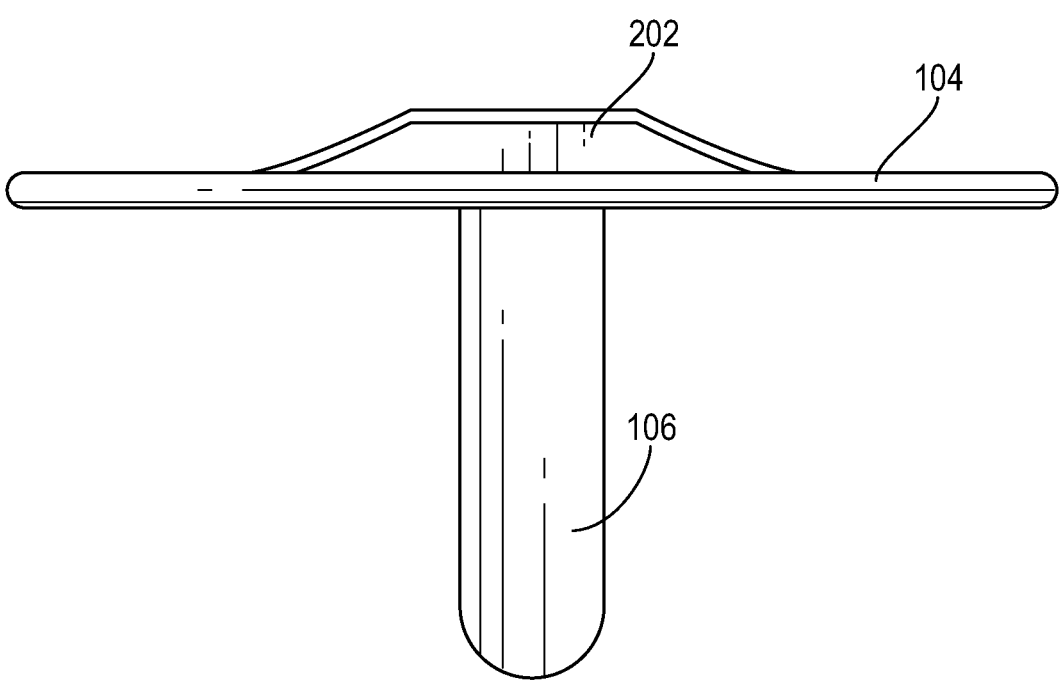
FIG. 2A is a perspective side view of a balloon assembly of the emergency protocol receptacle for puncture wounds, in accordance with embodiments of the invention.
Figure 2B:
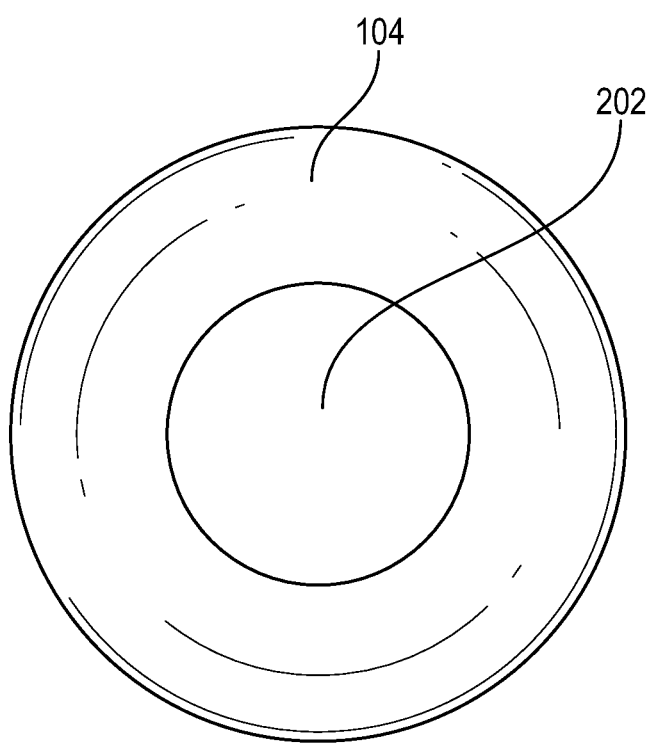
FIG. 2B is a perspective top view of the balloon assembly, in accordance with embodiments of the invention.
Figure 2C:
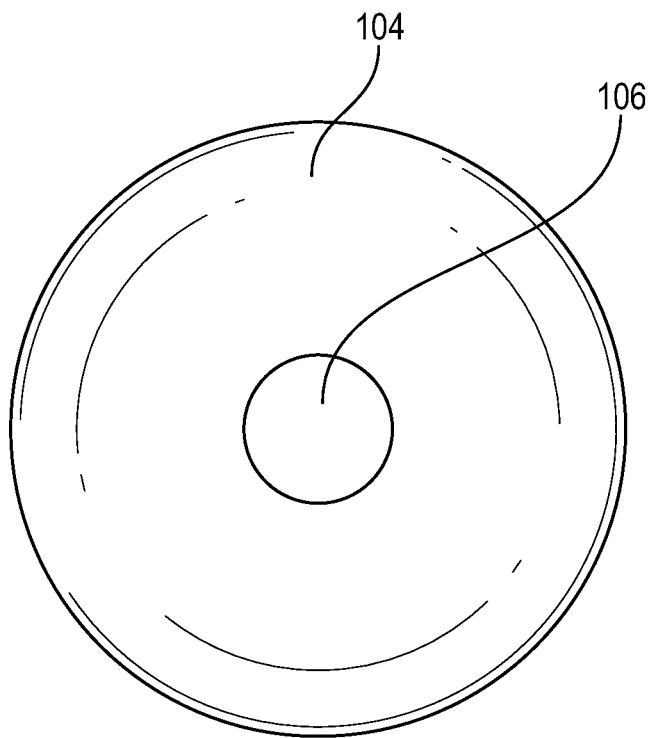
FIG. 2C is a perspective bottom view of the balloon assembly, in accordance with embodiments of the invention.

Referring to FIGS. 2A-2C, a balloon assembly 200 of the emergency protocol receptacle 100 is depicted. The balloon assembly 200 comprises the adhesive platform 104, and the balloon 106. The balloon 106 is attached at center of the adhesive platform 104, and the adhesive platform 104 is designed with an opening 202 at center. In specific, the balloon 106 is a transparent silicon balloon. The balloon 106 is configured to inflate due to chemical reaction caused by mixing of the vinegar and the baking soda. As the balloon 106 inflates, the bleeding is stopped from the puncture wound.

Figure 3A:
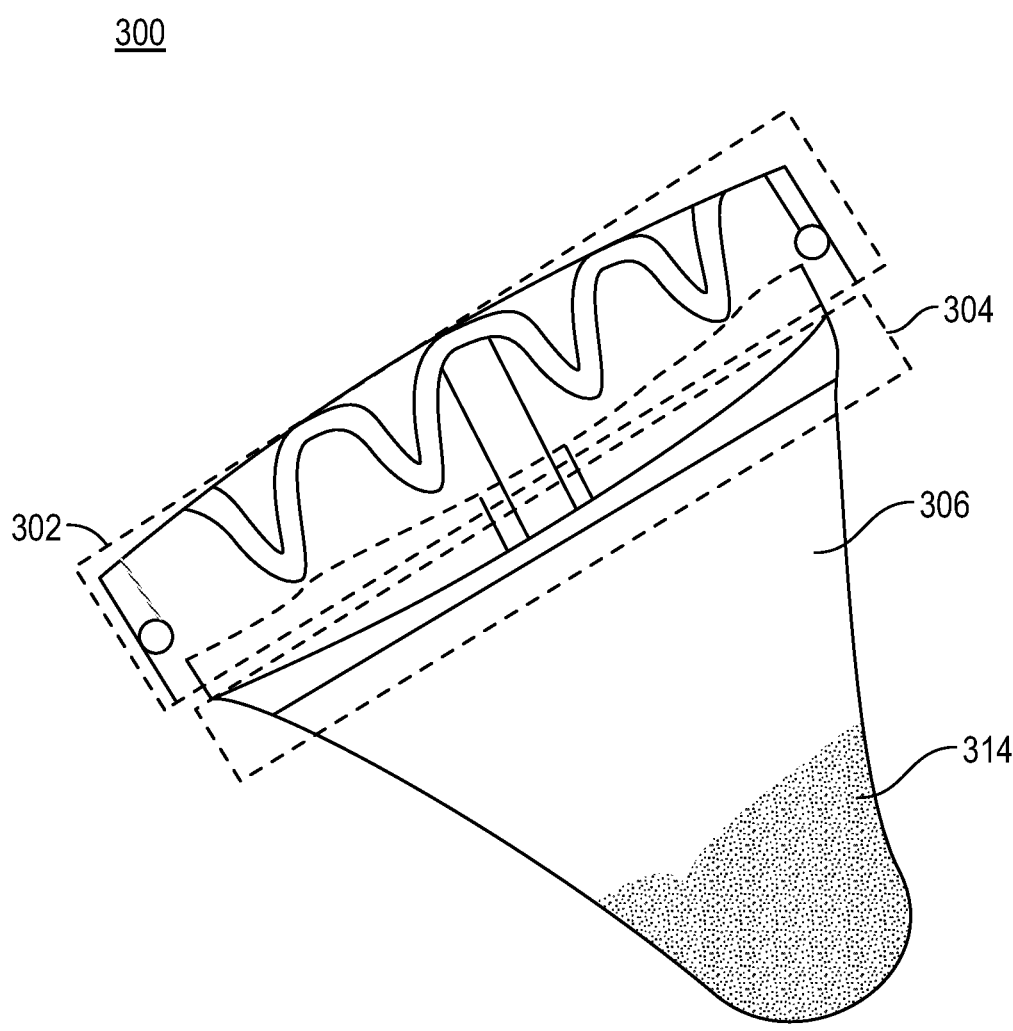
FIG. 3A is an assembled view of the powder capsule, in accordance with embodiments of the invention.
Figure 3B:
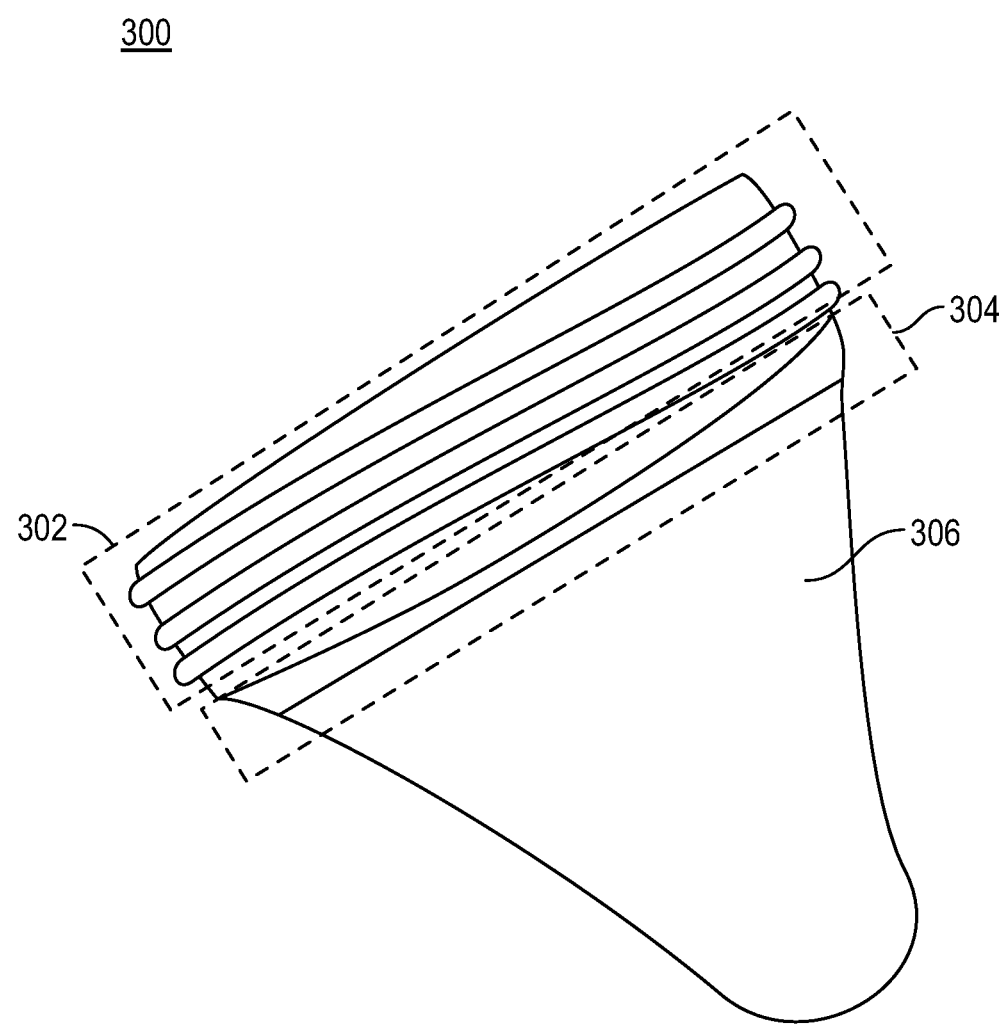
FIG. 3B is an assembled outline view of the powder capsule, in accordance with embodiments of the invention.
Figure 3C:
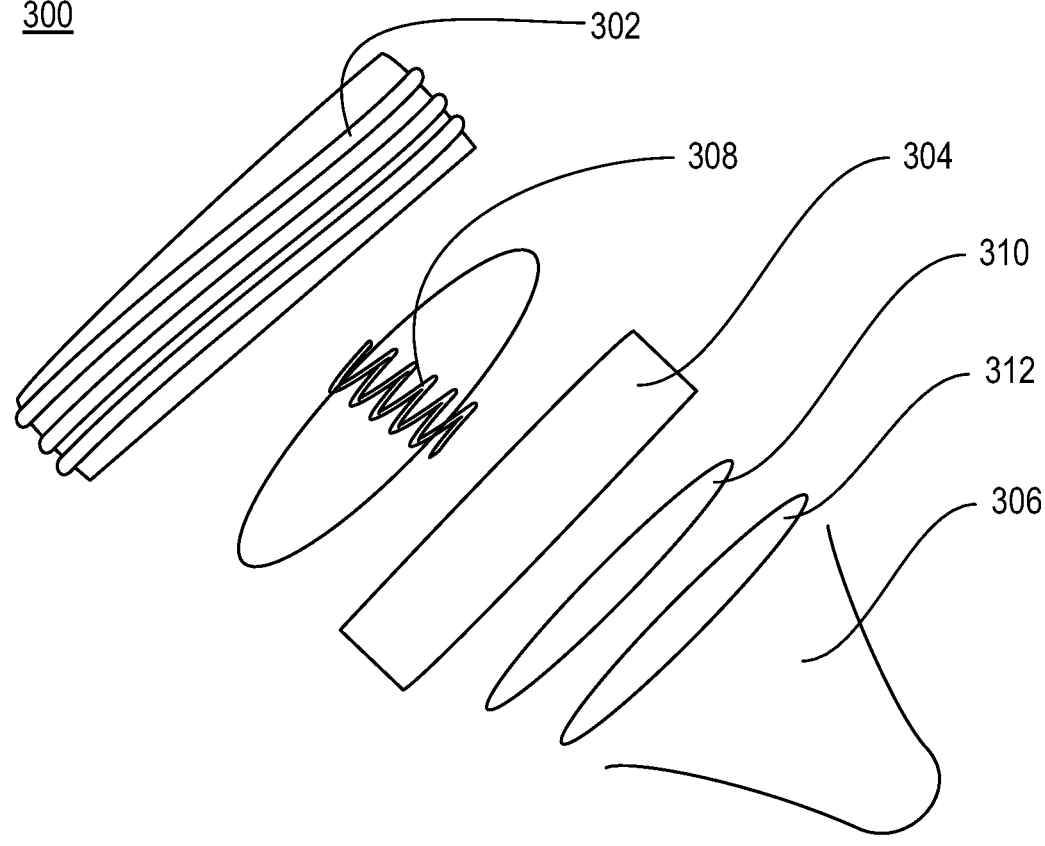
FIG. 3C is an exploded view of the powder capsule, in accordance with embodiments of the invention.

In another embodiment, FIG. 3A illustrates an assembled view of the powder capsule 300. FIG. 3B illustrates an assembled outline view of the powder capsule 300. FIG. 3C illustrates an exploded view of the powder capsule 300. The powder capsule 300 comprises a depressible top cap 302, a middle cap 304 and a powder pouch 306. The depressible top cap 302 is connected to the middle cap 304 through a spring 308. The spring 308 is configured to reduce the chance of accidental activation of the emergency protocol receptacle 100 by maintaining the depressible depressable top cap 302 separate from a foil divider 310. The powder pouch 306 is connected to the middle cap 304 using a holder ring 312. The holder ring 312 comprises a plurality of connecting means. The connecting means are configured to connect the powder pouch 306 to the middle cap 304.

Figure 4A:
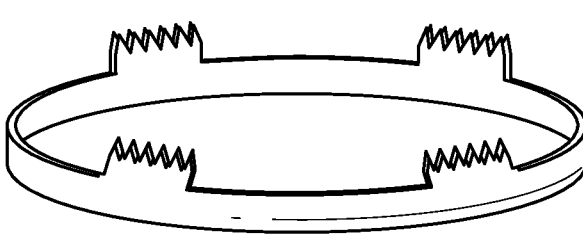
FIG. 4A illustrates a side tilted view of the holder ring, in accordance with embodiments of the invention.
Figure 4B:
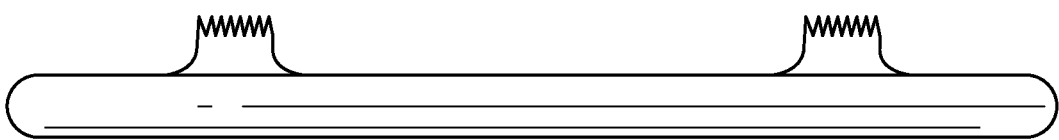
FIG. 4B illustrates a side view of the holder ring, in accordance with embodiments of the invention.
Figure 4C:
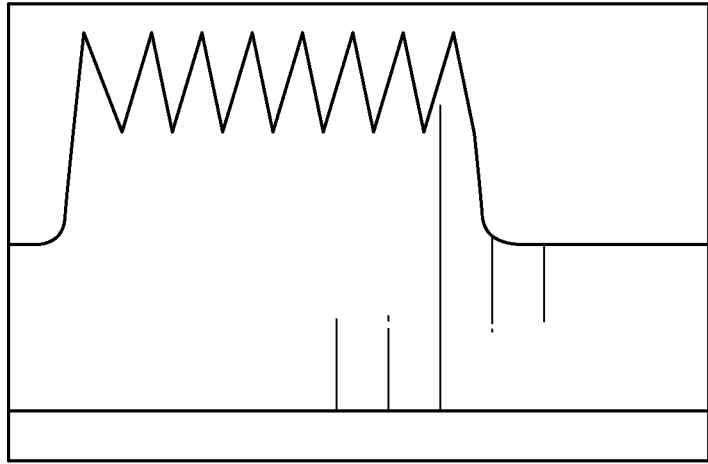
FIG. 4C illustrates a side zoomed view of the holder ring, in accordance with embodiments of the invention.
Figure 5A:
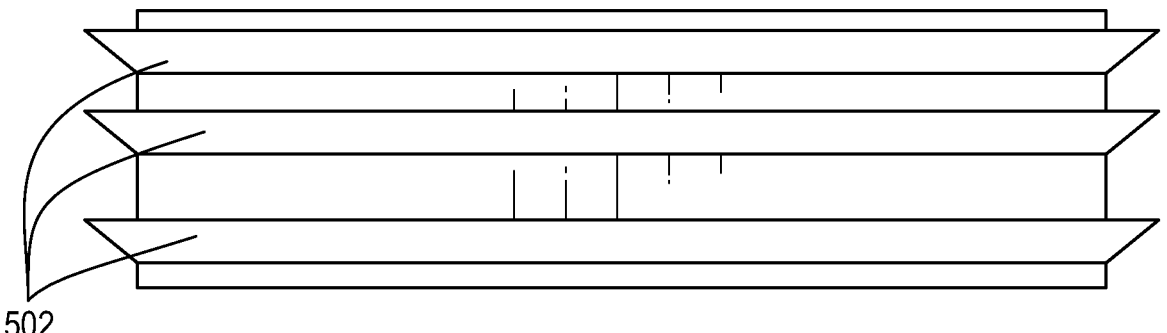
FIG. 5A is a side perspective view of a depressible top cap of a powder capsule of an emergency protocol receptacle, in accordance with embodiments of the invention.
Figure 5B:
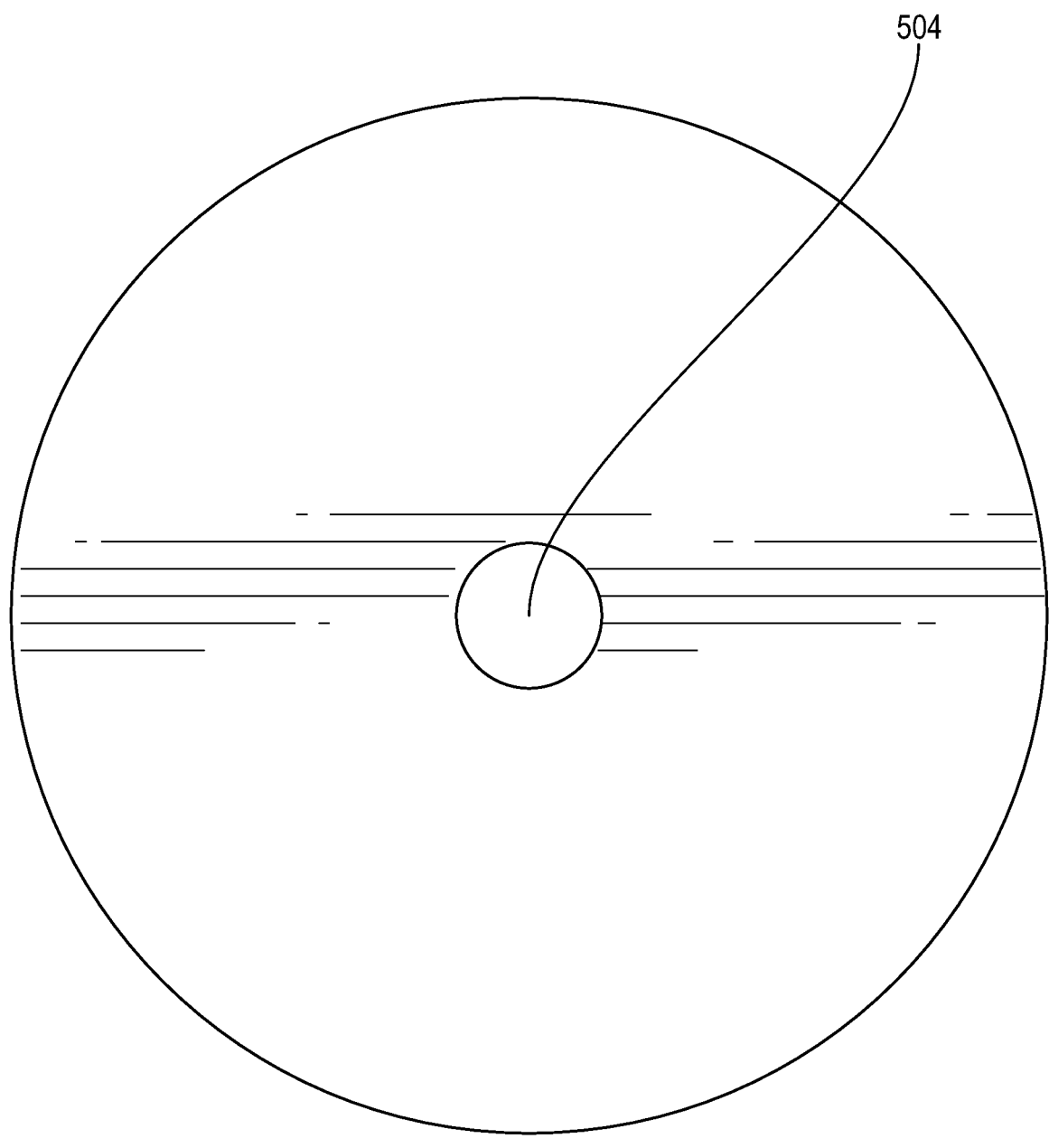
FIG. 5B is a top perspective view of the depressible top cap of the powder capsule, in accordance with embodiments of the invention.
Figure 5C:
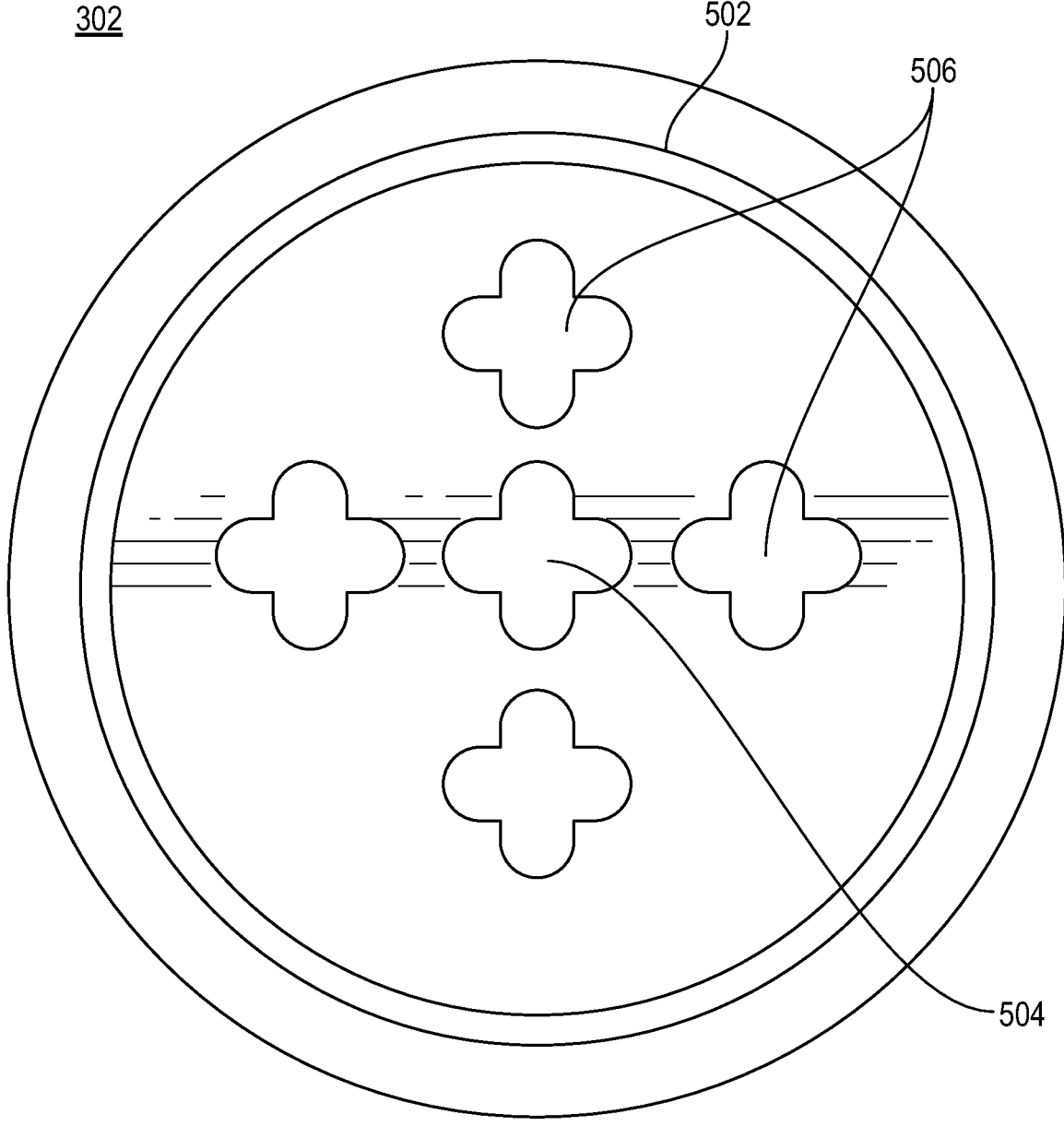
FIG. 5C is a perspective bottom view of the depressible top cap of the powder capsule with one or more spikes and a guide rail, in accordance with embodiments of the invention.
Figure 5D:
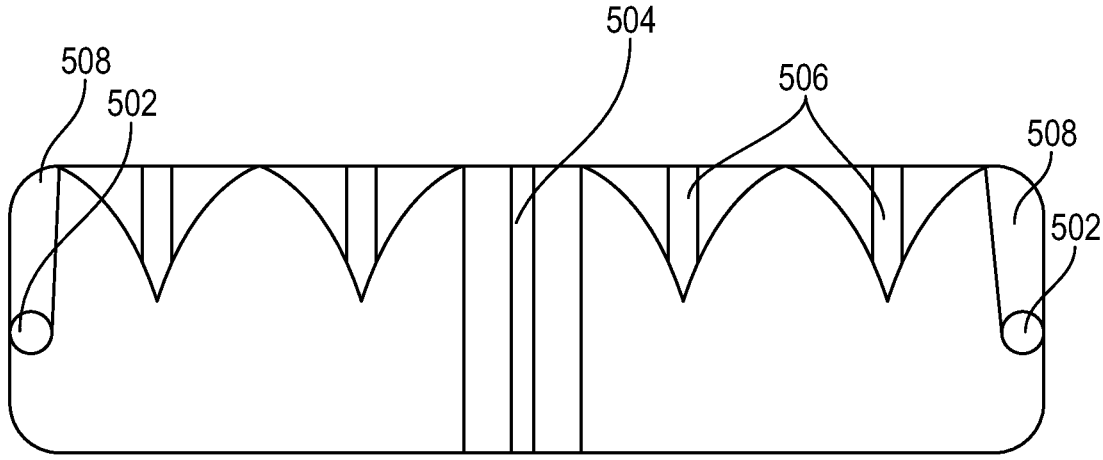
FIG. 5D is a cross-sectional view of the depressible top cap of the powder capsule, in accordance with embodiments of the invention.

In an embodiment, FIGS. 4A to 4C illustrate different views of the holder ring 312 with the connecting means.

FIG. 4A illustrates a side tilted view of the holder ring 312. FIG. 4B illustrates a side view of the holder ring 312. FIG. 4C illustrates a side zoomed view of the holder ring 312.

In one embodiment, the powder pouch 306 holds a specific amount of baking soda 314. In another embodiment, the powder pouch 306 is a woven square of cloth for holding the baking soda 314. The powder pouch 306 with the baking soda 314 placed inside the balloon for inflating the balloon when the baking soda 314 is mixed with the vinegar.

In one embodiment, a foil divider 310 is placed in between the middle cap 304 and the powder pouch 306 for separating the baking soda 314 and the vinegar. The foil divider 310 is punctured when pressure is applied on top of the depressible top cap 302 to allow the flow of the vinegar into the powder pouch 306.

As illustrated in FIGS. 5A through 5D, in a preferred embodiment, the depressible top cap 302 of the powder capsule 300 comprises a rubber gasket ring 502 around the circumference of the depressible top cap 302 to act as a seal for the vinegar. In one embodiment, the depressible top cap 302 comprises one or more spikes 506 and a guide rail 504. The spikes 506 are designed to protrude out from bottom of the depressible top cap 302. The guide rail 504 is designed to form a pass along a center of the depressible top cap 302 for allowing flow of a specific amount of vinegar. Further, the rubber gasket ring 502 is fixed on a ring mount ridge 508.

Figure 6A:
FIG. 6A is a perspective side view of a middle cap of the powder capsule of the emergency protocol receptacle, in accordance with embodiments of the invention.
Figure 6B:
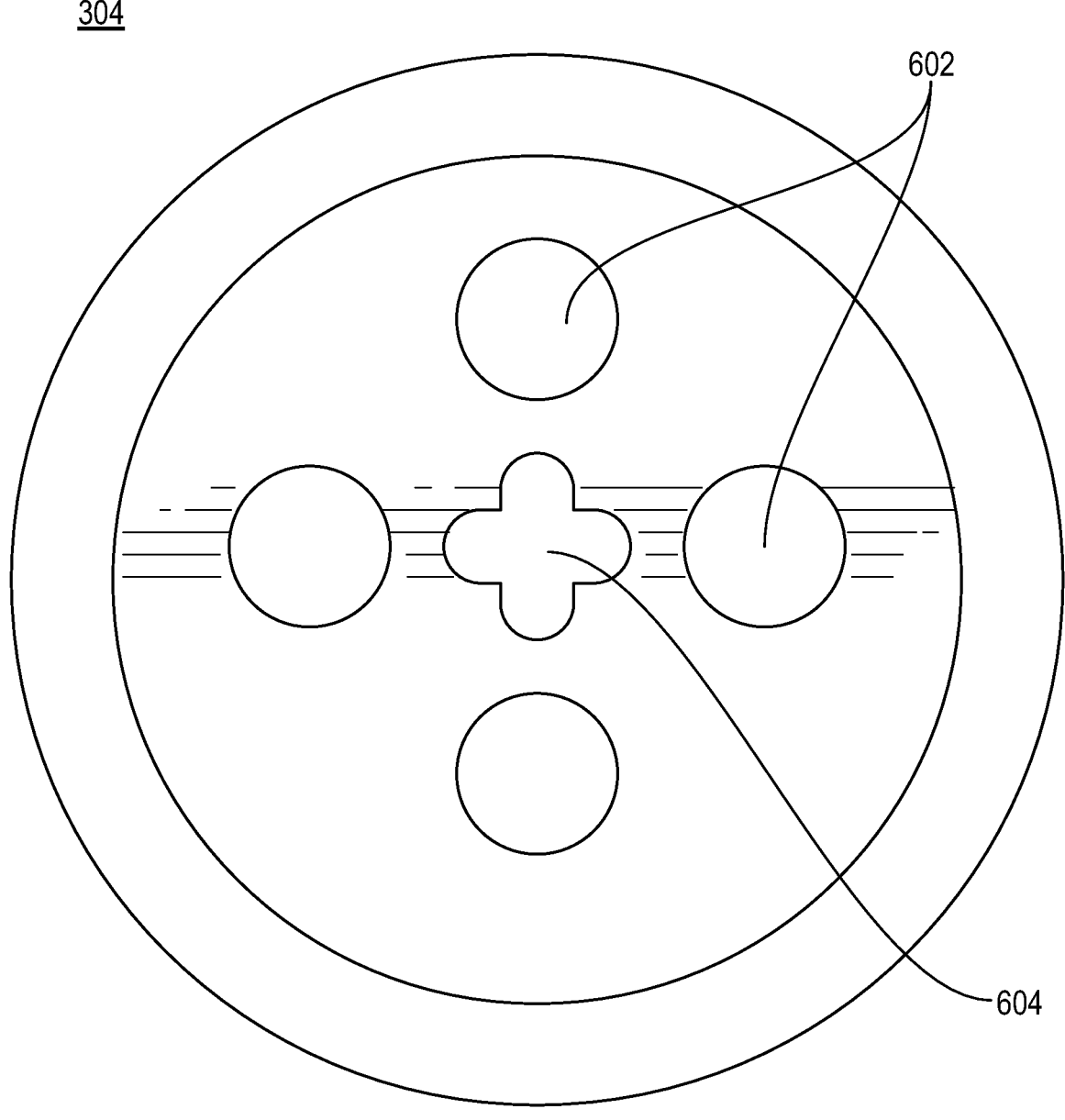
FIG. 6B is a top perspective view of the middle cap of the powder capsule, in accordance with embodiments of the invention.
Figure 6C:
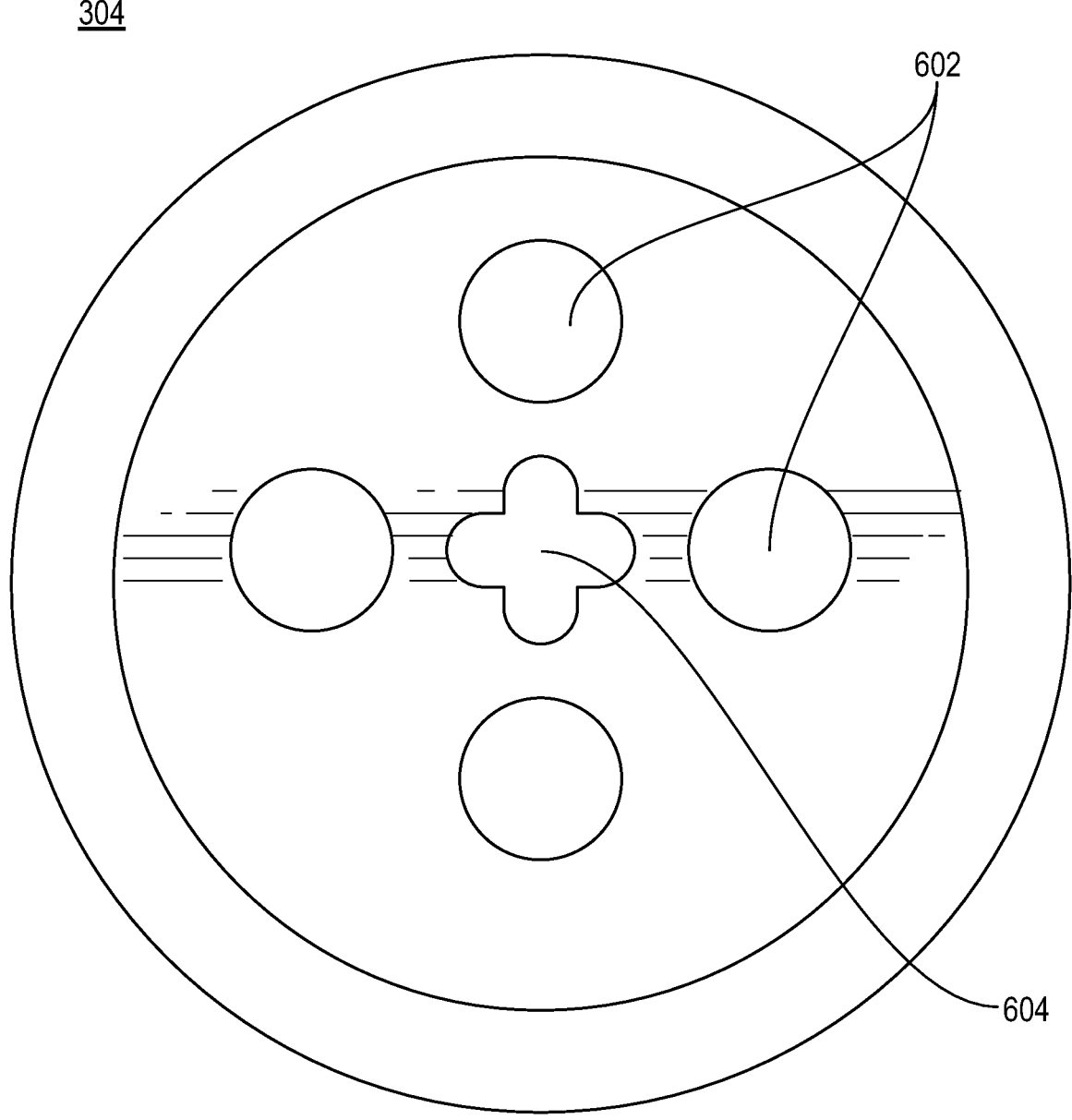
FIG. 6C is a perspective bottom view of the middle cap of the powder capsule with plurality of insertion holes, in accordance with embodiments of the invention.
Figure 6D:
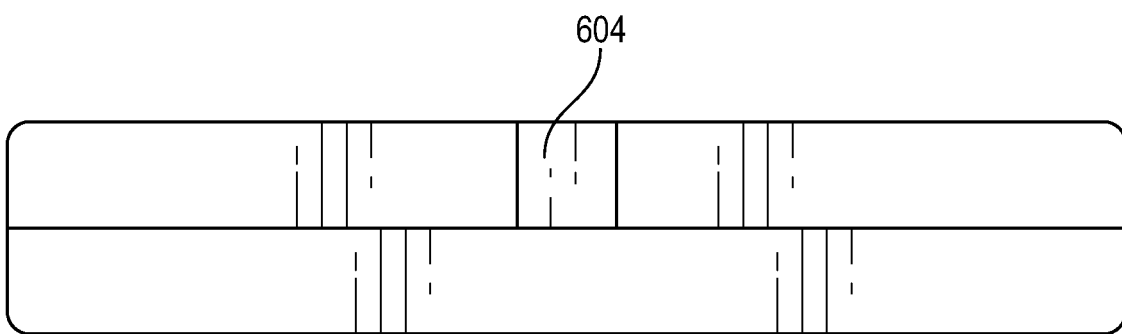
FIG. 6D is a cross-sectional view of the middle cap of the powder capsule with plurality of insertion holes, in accordance with embodiments of the invention.

Referring to FIGS. 6A through 6D, preferably, the middle cap 304 of the powder capsule 300 comprises a plurality of insertion holes (602, 604) that are configured to be in line with the spikes 506 and the guide rail 504 of the depressible top cap 302. FIG. 6A illustrates a side view of the middle cap 304. FIG. 6B illustrates a top view of the middle cap 304. FIG. 6C illustrates a bottom view of the middle cap 304. FIG. 6D illustrates a cross-sectional view of the middle cap 304.

In specific, the insertion holes comprise a rail insertion slot 604 at center to receive the guide rail 504 of the depressible top cap 302 to allow the flow of the vinegar. The insertion holes comprise a plurality of spike insertion holes 602 to receive the spikes 506 of the depressible top cap 302 for the flow of the vinegar.

In one embodiment, the middle cap 304 and the depressible top cap 302 are snap fit together by insertion of the guide rail 504 on the rail insertion slot 604 of the middle cap 304. The snap fit is provided by the precise fit of the dimensions of the guide rail 504 into the dimensions of the insertion hole 604. Similarly, the dimensions of the spikes 506 are same as that of the dimensions of the spike insertion holes 602.

In another embodiment, the foil divider 310 is punctured by the spikes 506 of the top cap 302 through the spike insertion holes 602 of the middle cap 304 when pressure is applied on top of the depressible top cap 302. This allows the vinegar to flow into the powder pouch 306 through the spike insertion holes 602 and the rail insertion slot 604.

Referring to FIG. 1, in accordance with embodiments of the invention, there is provided a prototype of the emergency protocol receptacle 100. The powder capsule 300 is inserted in the opening 202 of the adhesive platform 104. When pressure is applied on the depressible top cap 302, the spikes 506 of the depressible top cap 302 punctures the foil divider 310 for enabling the vinegar to mix with the baking soda in the powder pouch 306 to initiate inflation of the balloon 106 while inside a wound of the patient due to a chemical reaction between the vinegar and the baking soda.

Figure 7:
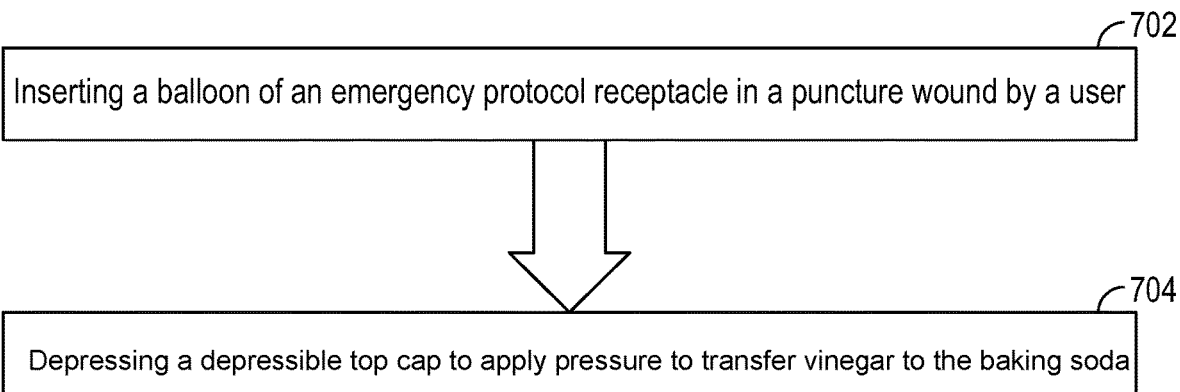
FIG. 7 is a method of using the emergency protocol receptacle for puncture wounds, in accordance with embodiments of the invention.

Referring to FIG. 7, in accordance with embodiments of the invention, there is provided a method 700 of using the emergency protocol receptacle 100. The emergency protocol receptacle 100 is first assembled by inserting the powder capsule 300 in the opening 202 of the adhesive platform 104. Vinegar is stored inside the depressible top cap 302 of the powder capsule 300 of the emergency protocol receptacle 100. The method 700 includes a step 702 for inserting the balloon 106 of the emergency protocol receptacle 100 in a puncture wound by a user. At step 704, pressure is applied by the user on the depressible top cap 302 of the powder capsule 300 with a squeezing or depressing action of the depressible top cap 302. Next, the spikes 506 of the depressible top cap 302 are enabled to puncture the foil divider 310 due to the pressure, which forms holes in the foil divider 310 for enabling the vinegar to fall in the powder pouch 306. Later, the vinegar reacts with the baking soda to initiate inflation of the balloon 106 due to chemical reaction between the vinegar and the baking soda. After the usage of the emergency protocol receptacle 100, the balloon 106 is deflated and is pulled out of the puncture wound.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation within the spirit and scope of the appended claims.

The claimed invention is:

1. An emergency protocol receptacle for puncture wounds, comprising:
   a balloon attached to an adhesive platform, wherein the adhesive platform defines an opening at a center thereof;
   a powder capsule packed inside the balloon through the opening of the adhesive platform, wherein the powder capsule holds a specific amount of baking soda; and
   a depressible top cap fixed on top of the powder capsule upon the adhesive platform, wherein the depressible top cap comprises a specific amount of vinegar, said depressible top cap adapted to transfer the specific amount of the vinegar into the powder capsule upon a depression of the depressible top cap by a user, wherein said transfer mixes the specific amount of the vinegar with the specific amount of baking soda to initiate inflation of the balloon due to a chemical reaction between the vinegar and the baking soda, wherein the inflated balloon is adapted to halts exsanguination in the puncture wound.

2. The emergency protocol receptacle as claimed in claim 1, wherein the balloon is a transparent silicon balloon.

3. The emergency protocol receptacle as claimed in claim 1, wherein the powder capsule comprises:
   the top cap comprising:
      a rubber gasket ring around a circumference of the top cap to act as a seal for the vinegar,
      one or more spikes, and
      a guide rail passing along a center of the top cap adapted to allow a flow of the vinegar;
   a middle cap comprising a plurality of insertion holes to connect with the one or more spikes and the guide rail of the top cap, and
   a powder pouch comprising a specific amount of baking soda, wherein the powder pouch is connected to the middle cap with a holder ring.

4. The emergency protocol receptacle as claimed in claim 3, wherein the plurality of insertion holes of the middle cap comprises a rail insertion slot at center to receive the guide rail of the top cap for the flow of the vinegar.

5. The emergency protocol receptacle as claimed in claim 3, wherein a foil divider is placed in between the middle cap and the powder pouch for separating the baking soda and the vinegar.

6. The emergency protocol receptacle as claimed in claim 5, wherein the foil divider is punctured by the one or more spikes of the top cap through the plurality of insertion holes of the middle cap, when pressure is applied on top of the top cap by the squeezing action of the depressible top cap to allow the flow of the vinegar into the powder pouch.

7. The emergency protocol receptacle as claimed in claim 3, wherein the top cap is connected to the middle cap through a spring, wherein the spring is configured to avoid accidental activation of the emergency protocol receptacle by maintaining the top cap separate from the foil divider.

8. The emergency protocol receptacle as claimed in claim 3, wherein the powder pouch is a woven square of cloth for holding the specific amount of baking soda.

\* \* \* \* \*